(12) United States Patent
Daliparthi et al.

(10) Patent No.: US 12,209,064 B2
(45) Date of Patent: Jan. 28, 2025

(54) ION-EXCHANGE RESIN CORE-SHELL CATALYST PARTICLES

(71) Applicant: SABIC GLOBAL TECHNOLOGIES B.V., Bergen Op Zoom (NL)

(72) Inventors: Surya Prakasa Rao Daliparthi, Bangalore (IN); Paulus Johannes Maria Eijsbouts, Nieuwkuijk (NL); Suman Kumar Sen, Bangalore (IN)

(73) Assignee: SABIC GLOBAL TECHNOLOGIES B.V., Bergen Op Zoom (NL)

( * ) Notice: Subject to any disclaimer, the term of this patent is extended or adjusted under 35 U.S.C. 154(b) by 754 days.

(21) Appl. No.: 17/290,375

(22) PCT Filed: Nov. 11, 2019

(86) PCT No.: PCT/EP2019/080783
§ 371 (c)(1),
(2) Date: Apr. 30, 2021

(87) PCT Pub. No.: WO2020/099285
PCT Pub. Date: May 22, 2020

(65) Prior Publication Data
US 2021/0403400 A1    Dec. 30, 2021

(30) Foreign Application Priority Data
Nov. 12, 2018   (EP) .................... 18205571

(51) Int. Cl.
*C07C 37/20* (2006.01)
*B01J 8/02* (2006.01)
(Continued)

(52) U.S. Cl.
CPC ............ *C07C 37/20* (2013.01); *B01J 8/0242* (2013.01); *B01J 21/08* (2013.01); *B01J 31/10* (2013.01);
(Continued)

(58) Field of Classification Search
CPC .. C07C 37/20; B01J 35/19; B01J 35/31; B01J 35/397; B01J 35/40; B01J 8/0242; B01J 21/08; B01J 31/10; B01J 37/0219
See application file for complete search history.

(56) References Cited

U.S. PATENT DOCUMENTS

| 3,922,255 A | 11/1975 | Koestler et al. |
| 5,233,096 A | 8/1993 | Lundquist |

(Continued)

FOREIGN PATENT DOCUMENTS

| CN | 102360659 A | * | 2/2012 |
| CN | 103272640 A | * | 9/2013 |

(Continued)

OTHER PUBLICATIONS

Patent No. CN 107970906 A, machine translation, May 2018, pp. 1-34. (Year: 2018).*

(Continued)

*Primary Examiner* — Richard M Rump
(74) *Attorney, Agent, or Firm* — CANTOR COLBURN LLP

(57) ABSTRACT

The invention is directed to a catalyst, to a method for manufacturing a catalyst, to a method for manufacturing a bisphenol compound, and to the use of a catalyst. The catalyst of the invention comprises particles having a core and a shell, wherein the shell comprises an ion exchange resin covering the core at least in part and wherein the core has a density that is higher than the density of the ion exchange resin.

14 Claims, 8 Drawing Sheets

(51) Int. Cl.
  *B01J 21/08* (2006.01)
  *B01J 31/10* (2006.01)
  *B01J 35/00* (2006.01)
  *B01J 35/30* (2024.01)
  *B01J 35/31* (2024.01)
  *B01J 35/40* (2024.01)
  *B01J 37/02* (2006.01)

(52) U.S. Cl.
  CPC ............... *B01J 35/19* (2024.01); *B01J 35/31* (2024.01); *B01J 35/397* (2024.01); *B01J 35/40* (2024.01); *B01J 37/0219* (2013.01)

(56) References Cited

U.S. PATENT DOCUMENTS

| | | |
|---|---|---|
| 5,288,926 A | 2/1994 | Patrascu et al. |
| 5,395,857 A | 3/1995 | Berg et al. |
| 6,730,816 B2 | 5/2004 | Lundquist |
| 10,537,865 B2 | 1/2020 | Daliparthi et al. |
| 2003/0013928 A1 | 1/2003 | Saruwatari |

FOREIGN PATENT DOCUMENTS

| | | | | |
|---|---|---|---|---|
| CN | 107722159 A | * | 2/2018 | ............... B01J 41/14 |
| CN | 107970906 A | * | 5/2018 | ............ B01J 21/063 |
| GB | 1401843 A | | 7/1975 | |
| WO | 9734688 A1 | | 9/1997 | |

OTHER PUBLICATIONS

Beyki, Mostafa Hossein, and Mohammad Hadi Ghasemi. "Quaternized γ-Fe2O3@ cellulose ionomer: an efficient recyclable catalyst for Michael-type addition reaction." International journal of biological macromolecules 113 (2018): 711-718.*

Gu et al., Preparation of Silica-Polystyrene Core Shell Particles up to Micron Sizes, 2004, Journal of Colloid and Interface Science 272, pp. 314-320.

International Search Report; International Application No. PCT/EP2019/080783; International Filing Date: Nov. 11, 2019; Date of Mailing: Jan. 30, 2020; 16 pages.

Li Qiao et al., "Magnetic nanospheres with molecularly imprinted shell for the prconcentration of diethylstilbestrol," 2014, vol. 181. No. 11-12, pp. 1341-1351.

Written Opinion; International Application No. PCT/EP2019/080783; International Filing Date: Nov. 11, 2019; Date of Mailing: Jan. 30, 2020; 16 pages.

* cited by examiner

ION-EXCHANGE RESIN CORE-SHELL CATALYST PARTICLES

CROSS-REFERENCE TO RELATED APPLICATION

This application claims the benefit of International Application Number PCT/EP2019/080783 filed on Nov. 11, 2019, which claims priority to European Patent Application Serial No. 18205571.5 filed Nov. 12, 2018. The related applications are incorporated herein in their entirety by reference.

TECHNICAL FIELD

The invention is directed to a catalyst, to a method for manufacturing a catalyst, to a method for manufacturing a bisphenol compound, and to the use of a catalyst. In particular, the invention relates to a catalyst for the manufacture of bisphenol compounds.

BACKGROUND

Ensuring that reacting species achieve optimal physical contact can be amount the most difficult challenges in the design of chemical reactors and catalyst. If done improperly, undesired by-products and an abundance of unreacted reactants can seriously erode the economics of the system. The employment of finely tuned catalyst can complicate reactor design and reaction control.

Bisphenols can generally be obtained by condensing a phenol with a ketone. For, example the industrial production of bisphenol A (2,2'-bis(4-hydroxyphenyl)propane, also known as p,p-BPA or simply BPA) involves a process wherein a mixture of excess phenol and acetone is passed through a cylindrical fixed-bed reactor filled with divinyl benzene cross-linked sulphonated polystyrene ion exchange resin catalyst. The direction of flow of the mixture may be either downwards or upwards as required by reactor design. Each feed direction has its own advantages and disadvantages. Typically, however, the flow of the viscous reactant mixture is down-flow.

When the feed direction is downwards, the pressure drop through the sulphonic acid resin catalyst bed is a major problem limiting the throughput of reactants and products, which ultimately limits the production of bisphenol A. The pressure drop can be caused, for example, by the viscosity and density of both reactants and products, particle size and particle size distribution of catalyst and the compressibility of the catalyst used. The compressibility of the sulphonic acid catalyst appears to be an important factor relating to the pressure drop level. The spherical catalyst particles can be compressed/deformed under pressure into a variety of non-spherical or lenticular shapes and a loss in bed void fraction, thereby leading to an exponential reduction in throughput.

U.S. Pat. No. 5,395,857, for example, describes a process in which the pressure loss in the industrial production of bisphenol A from acetone and phenol in a cylindrical fixed-bed reactor filled with sulphonic acid ion exchange resin in large quantities can be greatly limited. This is achieved by using a two layer catalyst bed in which at least one of the layers comprises an ion exchange resin catalyst which exhibits a 2% or lower degree of crosslinking.

Sometimes, it is more desirable or necessary to conduct reactions in the up-flow mode. An up-flow reactor would be desirable to allow the resin bed to stay uncompressed to take advantage of possible selective improvements. If one could effectively operate in the up-flow mode it would further be possible to employ reactors of much smaller size to achieve comparable throughput and selectivity improvement relative to those used in down-flow reactors due to significant reduction or elimination of pressure drop through the reactor. Nonetheless, operating in an up-flow mode has other disadvantages. One of these disadvantages is that the catalyst bed is not stable and that the up-flow operation results in significant back mixing/fluidisation. In particular, catalyst particles have the tendency to move, fluidise and/or mix in a vertical direction.

WO-A-97/34688 describes an up-flow reactor system for the production of bisphenol A, wherein the catalyst is an ion exchange resin catalyst that is fixed in a reactor bed. The reactor further comprises reactor packing that is randomly oriented with respect to the catalyst.

GB1401843 discloses a catalytic process in which the temperature of the reaction mixture reaches 120° C. or more, the catalyst comprising a graft copolymer having an inert polymeric nucleus of high thermal stability, and a layer of a polymer, which includes groups showing catalytic ability, of low thermal stability, the layer being grafted onto and surrounding, in shell form, the nucleus.

Qiao, Li & Gan, Ning & Hu, Futao & Wang, De & Lan, Hangzhen & Li, Tianhua & Wang, Hongfei. (2014). Magnetic nanospheres with a molecularly imprinted shell for the preconcentration of diethylstilbestrol. Microchimica Acta. 181. 1341-1351. 10.1007/s00604-014-1257-y. Qiao et al, discloses the preparation of magnetic nanoparticles coated with a surface implinted polymer for use in the preconcentration of diethylstilbestrol (DES). There remains a need in the art to improve catalysts, in particular for use in up-flow reactors.

BRIEF SUMMARY

In an aspect, a catalyst for the manufacture of a bisphenol from phenol and a ketone, comprising particles having a core and a shell, wherein the shell comprises an ion exchange resin covering the core at least in part and wherein the core has a density that is higher than the density of the ion exchange resin, wherein the core of the particles has a density of at least 2500 kg/m³.

In another aspect, A method for manufacturing a bisphenol compound, comprising reacting the phenol and the ketone in the presence of the catalyst.

In yet another aspect, a method for manufacturing a bisphenol comprising reacting a phenol and a ketone in the presence of an ion exchange resin catalyst, wherein the reaction is performed in an up flow reactor wherein the phenol and the ketone are fed to the reactor at an inlet and bisphenol is extracted at an outlet at a position higher than the inlet and wherein the catalyst comprises particles having a core and a shell, wherein the shell comprises an ion exchange resin covering the core at least in part and wherein the core has a density that is higher than the density of the ion exchange resin

DETAILED DESCRIPTION

Figure 1A:
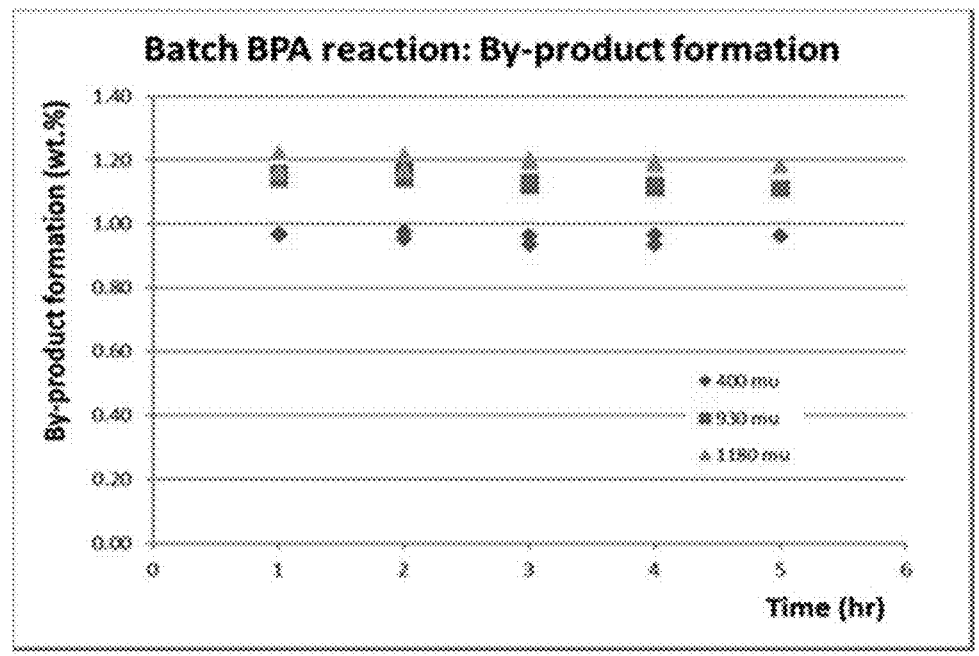
FIG. 1A is a graphical illustration of the by-product formation with time of Example 2.

Objective of the invention is to address this need and overcome or at least reduce one or more disadvantages of the prior art.

Further objective is to provide a catalyst that is highly suitable for use in an up-flow reactor, and in particular has uniform flow distribution.

Yet a further objective is to improve the catalyst bed stability with minimal or no back mixing in the reactor.

Yet a further objective is to provide a catalyst that allows stretching the operating space velocity in the reactor.

The inventors found that one or more of these objectives can, at least in part, be met by a specific core-shell catalyst.

Accordingly, in a first aspect the invention is directed to a catalyst comprising particles having a core and a shell, wherein the shell comprises an ion exchange resin covering the core at least in part and wherein the core has a density higher than the density of the ion exchange resin. More in particular the invention is directed to a catalyst for the manufacture of a bisphenol from phenol and a ketone comprising particles having a core and a shell, wherein the shell comprises an ion exchange resin covering the core at least in part and wherein the core has a density higher than the density of the ion exchange resin wherein the core of the particles has a density of at least 2500 kg/m3.

When a packed bed reactor is operated in an up-flow mode by introducing the feed at the bottom and withdrawing the products from the top of the reactor, the catalyst bed is subjected to fluidisation depending upon the feed flow rate. The density and size of the particles plays a major role to ensure catalyst bed stability. The particles are pulled down by gravitational force and at the same time fluid is flowing upwards by exerting a drag force on the catalyst particles. The higher the viscosity of the medium and the flow rate, the higher the drag force will be. The gravitational force depends on the particle density and particle size. If the particle has sufficient density and size to exert enough gravitational force to dominate the drag forces exerted by the fluid, the particle settles and remains in the reactor. If the gravitational force is significantly higher than the drag force, then the catalyst bed will be more stable.

For higher productivity, it is desired to operate the reactor at higher space velocity. This in turn leads to higher drag force on the catalyst particle and it may result in catalyst bed instability. In order to improve the catalyst bed stability, the particle size can be increased such that gravitational force increases and settling velocity increases. The inventors found, however, that the selectivity to make the desired p,p-BPA isomer reduces when increasing the catalyst particle size. This was attributed to diffusional resistance of the particle which increases by increasing the particle size.

The invention targets to increase the gravitational force by increasing the effective particle density (i.e. average density of the complete particle) and effective particle diameter (i.e. average diameter of the complete particle) by developing a core-shell type of catalyst particle. An inert high density material may be chosen for the core which is coated with an ion exchange resin shell. Since the core is made up of high density material it helps in improving the effective density of the catalyst particle. The overall particle size of the catalyst can be made bigger, because the catalyst is coated on the inert core particle. In this way both the effective density and particle size can be increased so as to increase the gravitational force, which in turn can help to improve the catalyst bed stability and allow high space velocity operation (which is usually limited by the density difference between the catalyst and the fluid). This type of catalyst particle does not negatively impact selectivity because the diffusional resistance is significantly reduced as the catalyst layer is relatively thin.

The catalyst particles comprise a core having a density that is higher than the ion exchange resin. The core can, for instance, comprise one or more selected from the group consisting of ceramics, silica (sand and glass), and metals.

Suitable ceramics include inorganic oxides (such as $Al_2O_3$, $Ce_2O$, $CeO_2$, $Ga_2O_3$, $GeO_2$, $HfO_2$, $La_2O_3$, $SiO_2$, $SnO_2$, $TiO_2$, $Y_2O_3$, $ZnO$, and $ZrO_2$), mixed inorganic oxides (such as $MgO/SiO_2$, and $CaO/Al_2O_3/SiO_2$), perovskites (such as $Ba—TiO_3$), spinels (such as $MgA_{12}O_4$ and $CoA_{12}O_4$), stabilised inorganic oxides (such as $Y_2O_3—ZrO_2$ and $La_2O_3—ZrO_2$), doped inorganic oxides with dopants such as Ce, Ti, La, Nb, Ta or F (such as cerium doped zirconia and fluorine doped tin oxide), and inorganic nitrides (such as silicon nitride, aluminium nitride, titanium nitride, and boron nitride).

Suitable metals include base metals (i.e. non-precious metals), precious metals, and any mixture of alloy thereof. Examples of base metals include transition metals, such as aluminium, chromium, cobalt, copper, iron, manganese, molybdenum, nickel, niobium, rhenium, tantalum, tin, titanium, tungsten, vanadium, zinc, zirconium, and/or any mixture or alloy thereof. Examples of precious metals include gold, iridium, osmium, palladium, platinum, rhodium, ruthenium, silver, and/or any mixture or alloy thereof. Some examples of suitable alloys include silver/gold, silver/palladium, silver/copper, and silver/tin.

Suitably, the core of the particles has an average particle diameter of 100 µm or more, such as 200 µm or more, 300 µm or more, 400 µm or more, 500 µm or more, 600 µm or more, or 700 µm or more. Suitably, the core of the particles has an average particle diameter of 1500 µm or less, such as 1200 µm or less, or 1000 µm or less. The average particle diameter of the core of the core-shell particles can be determined by, e.g. commonly known microscopy methods, automated imaging, laser diffraction and sieving techniques. For the avoidance of doubt it is noted that the average particle diameter and the average core diameter are to be understood as the number based averages. A sieving technique may be used to determine the diameter of the core of the particles to the extent the shell can be safely removed from the core prior to sieving. For example, in case the core of the catalyst is made from a metal the shell may be removed e.g. by chemical means, mechanical means or by combustion after which the diameter of the remaining core particles can be determined. A preferred microscopy method is SEM (Scanning Electron Microscopy).

As mentioned above the density of the core is higher than the density of the ion exchange resin present in the shell. Suitably, the core has a density of 2000 kg/m³ or more, preferably 2500 kg/m³ or more, such as 3000 kg/m³ or more. Suitably, the core has a density of 10000 kg/m³ or less, preferably 9000 kg/m³ or less, such as 8000 kg/m³ or less.

The shell of the catalyst particles can comprise a conventional ion exchange resin catalyst. These, for instance, include strong acid ion exchange resins, including resins or polymers having a plurality of appended sulphonic acid groups.

The introduction of sulphonic acid groups not only accomplishes sulfone crosslinking of the polymer but also yields catalysts containing polysulphonation in which the aromatic ring contains more than one sulphonic acid group per ring. In a preferred embodiment, the ion exchange comprises sulphone crosslinking.

Examples of suitable ion exchange resins include sulphonated polystyrene copolymers, sulphonated poly(styrene-divinyl-benzene) copolymers, and sulphonated phenol-formaldehyde resins. Specific examples of commercially available resins, for example, include Amberlite© or Amberlyst© manufactured by Rohm and Haas, Dowex© manufactured by Dow Chemical Company, Permutit QH© manufactured by Permutit Company, Chempro C-20© manufactured by Chemical Process Company.

Optionally, the shell can comprise a promoter, preferably a mercaptan compound. A mercaptan compound refers to a compound having a free form of SH group in the molecule. As the mercaptan, an alkyl mercaptan can be used (which may be a non-substituted alkyl mercaptan or an alkyl mercaptan having at least one substituting group, such as a carboxylic group, an amino group, a hydroxyl group, etc). Examples of non-substituted alkyl mercaptan include methyl mercaptan, ethyl mercaptan, n-butyl mercaptan, and n-octyl mercaptan. Examples of substituted alkyl mercaptan include mercaptocarboxylic acids (such as thioglycolic acid and β-mercaptopropionic acid), aminoalkane thiols (such as 2-amino ethane thiol and 2,2-dimethyl thiazolidine), and mercaptoalcohols (such as mercaptoethanol). Among these, the non-substituted alkyl mercaptans are preferred in terms of the promoting action. These mercaptans may be used singly or in combination. The promoter is attached to the ion exchange resin which allows the manufacture of bisphenols without the need for addition of a separate promoter.

For the preparation of bisphenol compounds, the amount of each of these mercaptans is generally selected to be in the range of 0.1-20 mol %, preferably in the range of 1-10 mol %, relative to acetone, which is one of the raw materials to be used.

The ion exchange resin may suitably have a density of 800 kg/m3 or more, such as 900 kg/m³ or more, or 1000 kg/m³ or more. The ion exchange resin may suitably have a density of 1500 kg/m³ or less, such as 1400 kg/m³ or less, or 1300 kg/m³ or less. Preferably, the difference in density between the core and the shell material is 500 kg/m³ or more, such as 750 kg/m³ or more, or 1000 kg/m³ or more. Typically, the difference in density between the core and the shell material does not exceed 8000 kg/m³. Preferably, the difference between the density of the core material and the density of the shell material is in the range of 500-7000 kg/m³, such as 750-6000 kg/m³, 1000-5000 kg/m³, 1200-4000 kg/m³, or 1400-3000 kg/m³.

The effective density of the overall core-shell particles of the catalyst of the invention can be in the range of 1000-4000 kg/m³, such as 1200-3400 kg/m³, preferably 1400-2800 kg/m³.

Suitably, the shell of the particles has an average layer thickness of 100 or more, such as 120 μm or more, or 150 μm or more. Suitably, the shell of the particles has an average layer thickness of 1000 μm or less, such as 800 μm or less, or 500 μm or less. The average layer thickness of the shell of the core-shell particles can be determined by, e.g., commonly known microscopy methods, automated imaging, laser diffraction and sieving techniques. A preferred method is SEM (Scanning Electron Microscopy). For the avoidance of doubt it is noted that several ways of determining the shell thickness exist and that a skilled person will have no difficulty in accurately determining the shell thickness. Thus, the average diameter of the catalyst particles can be determined as disclosed herein, the average being a numerical average. To the extent the shell material can be removed from the particles while leaving the core intact the difference between an average core diameter and an average particle diameter will allow determining the average layer thickness of the shell. Alternatively the shell material can be partially removed using e.g. mechanical techniques followed by determination of the layer thickness of the shell using microscopy. Preferably, the average layer thickness of the shell of the core-shell particles is relatively low, such as 400 μm less, more preferably 300 μm or less, even more preferably 200 μm or less, in order to increase selectivity of the catalyst and reduce formation of by-products.

The average particle diameter of the core-shell particles is preferably 200 μm or more, such as 300 μm or more, 400 μm or more, 500 μm or more, or 600 μm or more. The average particle diameter of the core-shell particles is preferably 2500 μm or less, such as 2200 μm or less, 2000 μm or less, 1800 μm or less, or 1600 μm or less. The average particle diameter of the core-shell particles can be determined by, e.g., commonly known microscopy methods, automated imaging, laser diffraction and sieving techniques. The average particle diameter is a numerical average. Preferably microscopy is used as the technique for determining the average particle diameter. A preferred method is SEM (Scanning Electron Microscopy). Preferably, the average particle size of the core-shell particles is relatively low, such as 1500 μm less, more preferably 1000 μm or less, even more preferably 800 μm or less, in order to increase selectivity of the catalyst and reduce formation of by-products.

The core-shell particles, as well as the particles forming the core are substantially spherical in shape meaning that a ratio D_max/D_min is in the range of from 0.85-1.15, preferably from 0.95-1.05, more preferably 0.98-1.02, wherein D_max is a maximum diameter measured on the particle and D_min a minimum diameter measured on the (core) particle. Generally D_max/D_min will be from 0.99-1.01. Most preferably D_max/D_min is 1.00.

The shell of the core-shell particles need not necessarily cover the core completely. For example, the shell may cover 50% or more of the surface area of the core, such as 60% or more, 70% or more, 80% or more, 90% or more, or 95% or more. Preferably, the core of the core-shell particles is completely covered with shell material.

Core-shell catalyst particles as described herein may be prepared in a number of different ways.

For example, raw material for the preparation of the ion exchange polymer (such as styrene, divinyl benzene and an initiator) can be mixed, suspended and polymerised as described, for instance, in U.S. Pat. Nos. 3,922,255, 5,233, 096, or EP-A-1 222 960. The procedure in the mentioned references may be further improvised to make core-shell particles as described here. Inert high density particles to be used as core can subsequently be wetted with the raw material mixture. For better adhesion, the raw material mixture may be slightly pre-polymerised. The wetted particles can then be dropped or injected into a column where aqueous medium is maintained at polymerisation temperature such that the raw material polymerises as the particles settle down the column. The residence time needed in the column is determined based on the polymerisation kinetics. Furthermore, the thickness of the raw material mixture on the inert particles can be optimised such that the material does not detach from the particles when being introduced into the column. The procedure may be repeated until the core-shell particles having a desired shell thickness. Finally, the polymer may be sulphonated in a usual manner to obtain sulphonated ion exchange catalyst.

According to yet another procedure to prepare core-shell particles as described herein, a polymer latex (such as a polystyrene divinyl benzene latex) is prepared using an emulsion polymerisation method. Inert high density particles are put in a rotavap or any rotating device with internal baffles for mixing (or a fluidised bed coating system). The latex can subsequently be introduced into the rotary mixing device or fluid bed granulator in a controlled fashion such that the latex is coated on the inert particles. Once the solvent is removed, the procedure may be repeated until the core-shell particles having a desired shell thickness are obtained. In order to improve the integrity of the particle, the obtained core-shell particles may be soaked in monomer mixture and further dropped into a water column/agitated vessel where water is maintained at polymerisation temperature such that additional polymerisation in void spaces provides more mechanical strength to the core-shell catalyst particle. In a further step, the polymer may be sulphonated in a usual manner to obtain sulphonated ion exchange catalyst.

Another procedure to make core-shell particles is described by Gu et al. (*Journal of Colloid and Interface Science* 2004, 272(2), 314-320). Although the original article applies this dispersion polymerisation based method to prepare nano-sized core-shell particles (800-1500 nm), the method may be applied to prepare micron sized core-shell catalyst particles (400-1500 μm).

In a further aspect, the invention therefore directed to a method for manufacturing a catalyst according to the invention, comprising the steps of providing core particles and covering an outside surface of the particles at least in part with an ion exchange resin, wherein said core particles have a density that is higher than the density of the ion exchange resin. As described above, such method may involve one or more of coating the core particles with ion exchange resin using in-situ polymerisation, and coating the core particles with ion exchange resin using a latex prepared by emulsion polymerisation.

In a further aspect, the invention is directed to a method for manufacturing a bisphenol compound, comprising reacting a phenol with a ketone in the presence of a catalyst of the invention.

Preferably, in said method the reaction is performed in an up-flow reactor, wherein the reactants are fed to the reactor at an inlet and bisphenol compound is extracted at an outlet at a position higher than the inlet.

The bisphenol compound may, for instance, be bisphenol A (2,2'-bis(4-hydroxyphenyl)propane), bisphenol S (4,4'-sulphonyldiphenol), or bisphenol F (4,4'-dihydroxydiphenylmethane). Preferably, the bisphenol compound is bisphenol A.

The molar ratio of phenol to acetone is usually in the range of 3-30 mol of phenol per mol of acetone, and preferably 5-15 mol of phenol per mol of acetone. If the molar ratio is smaller than 3 mol of phenol per mol of acetone, then the reaction speed is likely to be too slow. If it molar ratio is larger than 30 mol of phenol per mol of acetone, then the System becomes too dilute to have commercial significance.

Typically, the reaction temperature may be 40-150° C., preferably 60-110° C., more preferably 50-100° C. Temperatures of at most 100° C. are preferred in view of selectivity of the reaction. The reaction may be performed batch-wise or continuously. Preferably, the reaction is performed in a fixed bed continuous reactor in which phenol and ketone (such as acetone) are continuously fed into a reactor filled with the catalyst of the invention to react them. The reactor may be a single reactor, or may be two or more reactors that are connected in series. Optionally, the reaction mixture is subjected to a step for removing unreacted ketone, and water, e.g. by distillation. Such optional distillation may be performed under reduced pressure using a distillation column. In general such distillation is carried out at a pressure of 6.5-80 kPa and at a temperature of 70-180° C. Unreacted phenol then boils by azeotropy, and part thereof is removed. The bisphenol product may be concentrated by further removal of phenol. Such further distillation may typically be performed at 100-170° C. and a pressure of 5-70 kPa.

In yet a further aspect, the invention is directed to the use of a catalyst according to invention in a catalyst bed of an up-flow reactor. As described herein, the catalyst of the invention can advantageously be used in an up-flow reactor. The catalyst of the invention increases bed stability, minimises back mixing, and allows to operate the reactor at higher space velocity.

All references cited herein are hereby completely incorporated by reference to the same extent as if each reference were individually and specifically indicated to be incorporated by reference and were set forth in its entirety herein.

The use of the terms "a" and "an" and "the" and similar referents in the context of describing the invention (especially in the context of the claims) are to be construed to cover both the singular and the plural, unless otherwise indicated herein or clearly contradicted by context. The terms "comprising", "having", "including" and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention. For the purpose of the description and of the appended claims, except where otherwise indicated, all numbers expressing amounts, quantities, percentages, and so forth, are to be understood as being modified in all instances by the term "about". Also, all ranges include any combination of the maximum and minimum points disclosed and include and intermediate ranges therein, which may or may not be specifically enumerated herein.

Preferred embodiments of this invention are described herein. Variation of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject-matter recited in the claims appended hereto as permitted by applicable law. Moreover, any combination of the above-described elements in all possible variations thereof is encompassed by the invention unless otherwise indicated herein or otherwise clearly contradicted by context. The claims are to be construed to include alternative embodiments to the extent permitted by the prior art.

For the purpose of clarity and a concise description features are described herein as part of the same or separate embodiments, however, it will be appreciated that the scope of the invention may include embodiments having combinations of all or some of the features described.

The invention will now be further illustrated by the following non-limiting examples.

EXAMPLES

In order to establish the benefit of using this type of catalyst particle to improve catalyst bed stability, calculations are done to prove the high space velocity operability of the core-shell catalyst using the Ergun equation. Multiphase Computational Fluid Dynamics (CFD) simulations were also done with normal 550 μm diameter catalyst particles and 1000 μm diameter core-shell type catalyst particles.

Example 1

In this example, different catalyst particles were compared for their bed suspension velocity and minimum fluidisation velocity using the following equation generated by equating the Ergun equation pressure drop to the catalyst bed weight $$\frac{150 \mu V_{mf}}{D_p^2} \frac{(1-\epsilon_{mf})}{\epsilon_{mf}^3} + \frac{1.75 \rho V_{mf}^2}{D_p^2} \frac{1}{\epsilon_{mf}^3} = g(\rho_p - \rho)$$

wherein $V_{mf}$ is the minimum fluidisation velocity, $\epsilon_{mf}$ is the voidage at minimum fluidisation velocity, $\mu$ is the viscosity of the fluid, $\rho$ is the density of the fluid, $\rho_p$ is the density of the particles, $D_p$ is the diameter of the particles, and g is the gravitational constant.

The calculation results are shown in table 1. This table displays three velocities: the bed suspension velocity, the minimum fluidisation velocity for an assumed voidage at minimum fluidisation of 0.4, and the minimum fluidisation velocity for an assumed voidage at minimum fluidisation of 0.45. Typically, most of the particles, fluidise between 0.4 and 0.45 voidage. Therefore, the velocities for these two limits are shown in Table 4. However, the most important velocity is bed suspension velocity for which a bed voidage of 0.35 is used in the calculation.

For every column in table 1, the gravitational force on the catalyst bed dominates the pressure drop and the catalyst bed behaves more like a fixed bed, until the bed suspension velocity is tried at the inlet. Once this velocity is exceeded, the gravitational force is dominated by the pressure drop, and the catalyst bed gets suspended by the fluid and the catalyst particles start moving freely in the bed and leads to bed expansion. Upon further raising the inlet velocity, eventually fluidisation will start.

For the different cases in table 1 (comparative examples and inventive examples), the bed suspension velocities can be compared. For example, the base case 550 μm particles bed (comparative, column 2) suspends at a velocity of 0.00010 m/s (corresponding to a weight hour space velocity (WHSV) of 0.8). By just increasing the particle size to 1000 μm (i.e. base case 1000 μm; comparative, column 3), the bed suspension velocity can be increased to 0.0003 m/s (corresponding to a WHSV of 2.6). However, with 1000 μm core-shell catalyst particles of the invention (column 6), it is possible to significantly increase the bed suspension velocity to 0.001 m/s (corresponding to a WHSV of 8). Hence, with the core-shell catalyst of the invention, the operating window is raised up to a WHSV of 8 without a penalty on the selectivity.

Additionally, minimum fluidisation velocities were calculated and converted into WHSV by assuming two different voidages of 0.4 and 0.45, respectively. A WHSV of 1 is defined as linear liquid velocity of 0.000132 m/s. The results are also shown in table 1. These results show that with conventional catalyst (column 2) at a WHSV of 2, channelling and fluidisation is very likely. Core-shell catalyst particles of the invention provide a broad operating space before fluidisation starts.

Similar calculations were done with a different arbitrary catalyst density of 1235 kg/m³ and shown in columns 4 and 5 with a particle size of 550 μm and 1000 μm, respectively. The corresponding core-shell catalyst calculations are shown in column 7. Calculations in column 6 and 7 assume silica sand as the core. Column 8 is the same as column 6, except that steel is used as core material. As shown in table 1, by changing the core material from silica sand (column 6) to steel (column 8), the bed suspension velocity is increased from 0.001 m/s to 0.0035 m/s.

TABLE 1

| Description | Base case (550 μm) | Base case (1000 μm) | Base case (550 μm) | Base case (1000 μm) | Core-Shell Catalyst | Core-Shell Catalyst | Core-Shell Catalyst |
|---|---|---|---|---|---|---|---|
| core material | | | | | silica | silica | steel |
| core diameter (μm) | | | | | 600 | 600 | 600 |
| core volume (m³) | | | | | $1.13 \times 10^{-10}$ | $1.13 \times 10^{-10}$ | $1.13 \times 10^{-10}$ |
| core density (kg/m³) | | | | | 2650 | 2650 | 7820 |
| core mass (kg) | | | | | $3.00 \times 10^{-7}$ | $3.00 \times 10^{-7}$ | $8.84 \times 10^{-7}$ |
| shell volume (m³) | | | | | $4.10 \times 10^{-10}$ | $4.10 \times 10^{-10}$ | $4.10 \times 10^{-10}$ |
| shell density (kg/m³) | | | | | 1182 | 1235 | 1182 |
| shell mass (kg) | | | | | $4.85 \times 10^{-7}$ | $5.07 \times 10^{-7}$ | $4.85 \times 10^{-7}$ |
| shell thickness (μm) | | | | | 200 | 200 | 200 |

TABLE 1-continued

| Description | Base case (550 μm) | Base case (1000 μm) | Base case (550 μm) | Base case (1000 μm) | Core-Shell Catalyst | Core-Shell Catalyst | Core-Shell Catalyst |
|---|---|---|---|---|---|---|---|
| particle diameter (μm) | 550 | 1000 | 550 | 1000 | 1000 | 1000 | 1000 |
| total volume (m$^3$) | | | | | $5.23 \times 10^{-10}$ | $5.23 \times 10^{-10}$ | $5.23 \times 10^{-10}$ |
| total mass (kg) | | | | | $7.85 \times 10^{-7}$ | $8.06 \times 10^{-7}$ | $1.37 \times 10^{-7}$ |
| catalyst volume (m$^3$) | | | | | $4.10 \times 10^{-10}$ | $4.10 \times 10^{-10}$ | $4.10 \times 10^{-10}$ |
| overall/effective density (kg/m$^3$) | 1182 | 1182 | 1235 | 1235 | 1499 | 1541 | 2616 |
| liquid density (kg/m$^3$) | 1032 | 1032 | 1032 | 1032 | 1032 | 1032 | 1032 |
| liquid viscosity (kg/m · s) | 0.0019 | 0.0019 | 0.0019 | 0.0019 | 0.0019 | 0.0019 | 0.0019 |
| Minimum Velocity for bed suspension | | | | | | | |
| bed voidage | 0.35 | 0.35 | 0.35 | 0.35 | 0.35 | 0.35 | 0.35 |
| minimum velocity for bed suspension (m/s) | 0.00010 | 0.0003 | 0.00014 | 0.0005 | 0.0010 | 0.0011 | 0.0035 |
| WHSV for bed suspension | 0.8 | 2.6 | 1.1 | 3.5 | 8.0 | 8.7 | 26.4 |
| Minimum Fluidisation Calculations | | | | | | | |
| voidage at minimum fluidisation (assumed) | 0.4 | 0.4 | 0.4 | 0.4 | 0.4 | 0.4 | 0.4 |
| velocity at minimum fluidisation (m/s) | 0.00017 | 0.0005 | 0.00023 | 0.0007 | 0.0017 | 0.0018 | 0.0055 |
| WHSV at minimum fluidisation | 1.3 | 4.1 | 1.7 | 5.6 | 12.8 | 13.9 | 41.6 |
| voidage at minimum fluidisation (assumed) | 0.45 | 0.45 | 0.45 | 0.45 | 0.45 | 0.45 | 0.45 |
| velocity at minimum fluidisation (m/s) | 0.00026 | 0.0008 | 0.00035 | 0.0011 | 0.0026 | 0.0028 | 0.0082 |
| WHSV at minimum fluidisation | 2.0 | 6.4 | 2.6 | 8.7 | 19.6 | 21.3 | 62.5 |
| Benefits on selectivity | N/A | No | N/A | No | Yes | Yes | Yes |

Example 2

Bisphenol A was synthesised using ion exchange resin catalysts of different particle size (measured on fresh catalyst, as opposed to in phenol where the effective particle size is smaller due to shrinkage). Reacting conditions using monodisperse ion exchange resin catalysts in batch bisphenol A reactions were: temperature of 75° C., 4 wt. % of acetone, 100 g phenol, 6 g catalyst and 1300 ppm SH.

Figure 1B:
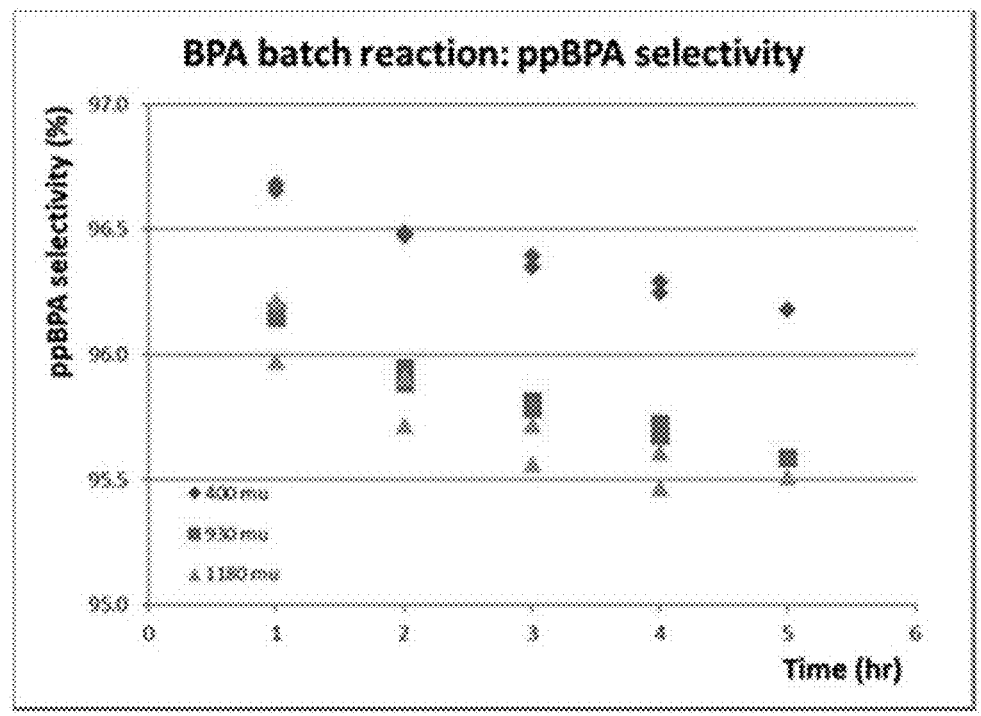
FIG. 1B is a graphical illustration of the ppBPA selectivity with time of Example 2.

The results are shown in FIGS. 1A and 1B. The data show that with particles of around 400 μm diameter (or diffusion layer of about 200 μm) the by-product formation was about 25% less compared to the bigger particles, i.e. the commercial size materials (around 1000 μm). From this data the present inventors were able to determine a desired layer thickness of the shell.

Comparative CFD Example

Figure 2:
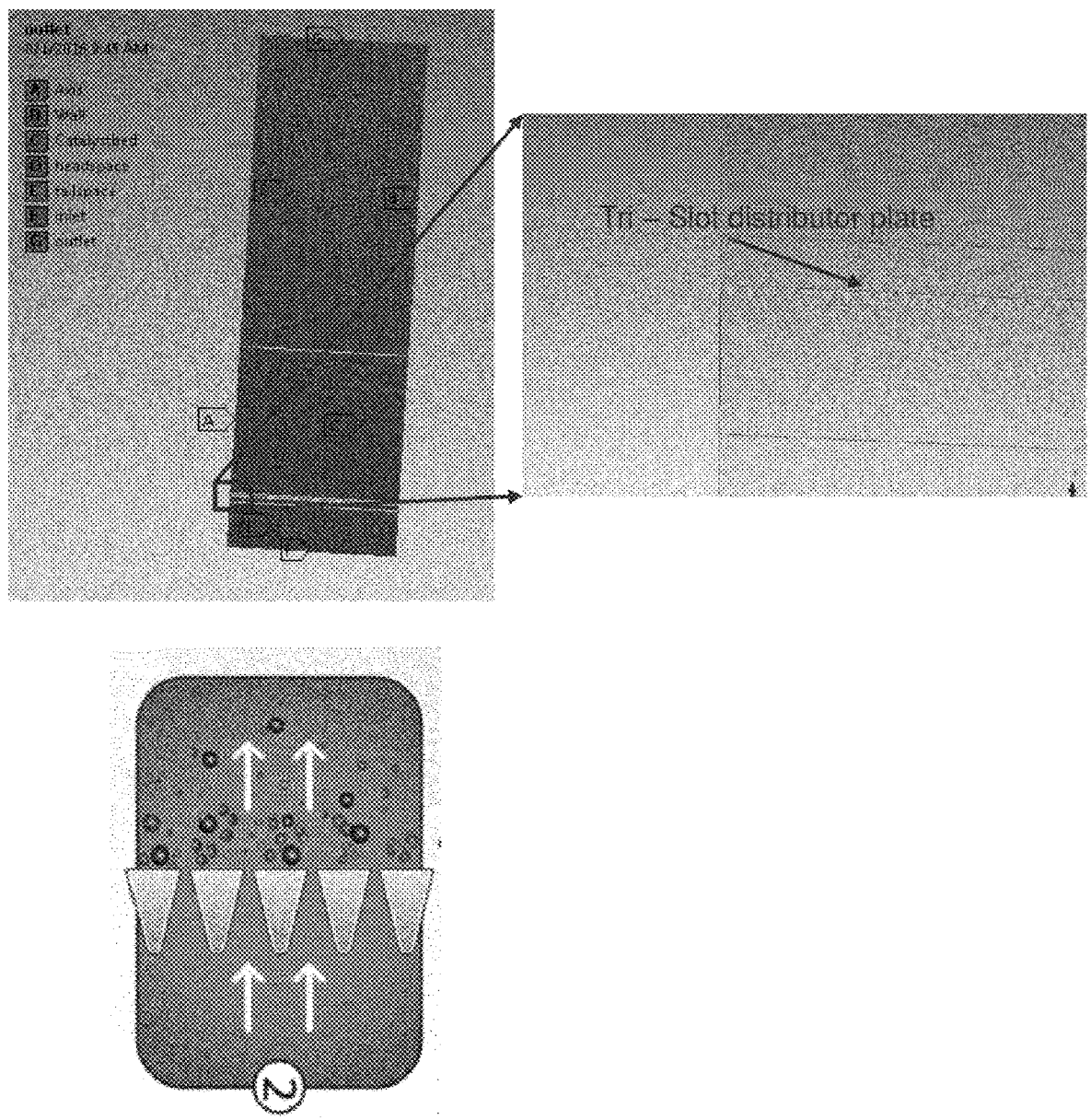
FIG. 2 is an illustration of an aspect of an up-flow reactor.

Multiphase Computational Fluid Dynamics (CFD) simulations were done using ANSYS FLUENT 17.1 with Eulerian-Eulerian multiphase simulation framework and laminar flow model. Gidaspow drag law was used to model solid-liquid interaction. Granular viscosity is modelled using Gidaspow model (Frictional viscosity not modelled). CFD simulations were done in a single stage up-flow reactor using 550 μm ion exchange resin catalyst particle size. Simulation conditions are shown in table 2. A WHSV of 2 corresponds to a superficial velocity of 0.000264 μm/s. One section of the up-flow reactor was modelled as shown in FIG. 2. Half of the section was modelled due to the available symmetry with respect to the vertical axis "A". Inlet, outlet, catalyst bed, distributor plate, etc. are as shown in FIG. 2. In the figure, "tail space" means below distributor plate. The distributor plate is modelled as is (tri-slot distributor). The distributor plate basically has 1.8 mm width bars with 0.2 mm clearance between them. The model uses a constant velocity inlet at the bottom of the up-flow reactor.

TABLE 2

| Condition | Value |
|---|---|
| Catalyst particle density | 1182 kg/m$^3$ |
| Feed density | 1032 kg/m$^3$ |
| Feed viscosity | 0.0019 Pa · s |
| Feed velocity at inlet | 0.000264 m/s |
| Initial bed voidage | 0.35 |

Figure 3:
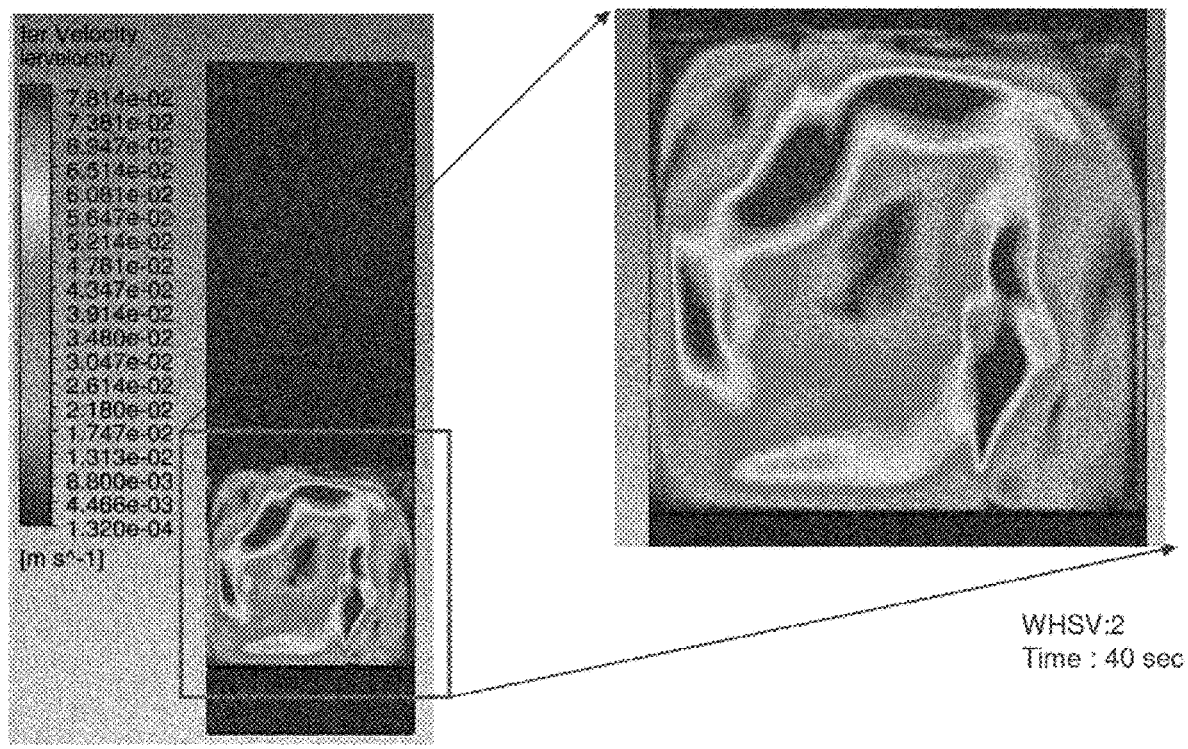
FIG. 3 is an illustration of the velocity contours of the ion exchange resin particles in the catalyst bed of the CFD example.

Multiphase CFD simulations were done in a transient mode and the results at 40 seconds simulation time are discussed here. Velocity contours of the ion exchange resin particles in the catalyst bed are shown in FIG. 3. It can be noted from the contours that a strong channels were formed and the reaction mass is likely to escape through this path leading to lower residence time and lower conversion. It is also observed that significant back mixing is expected due to these profiles and a true plug flow behaviour was not possible under these conditions.

Figure 4:
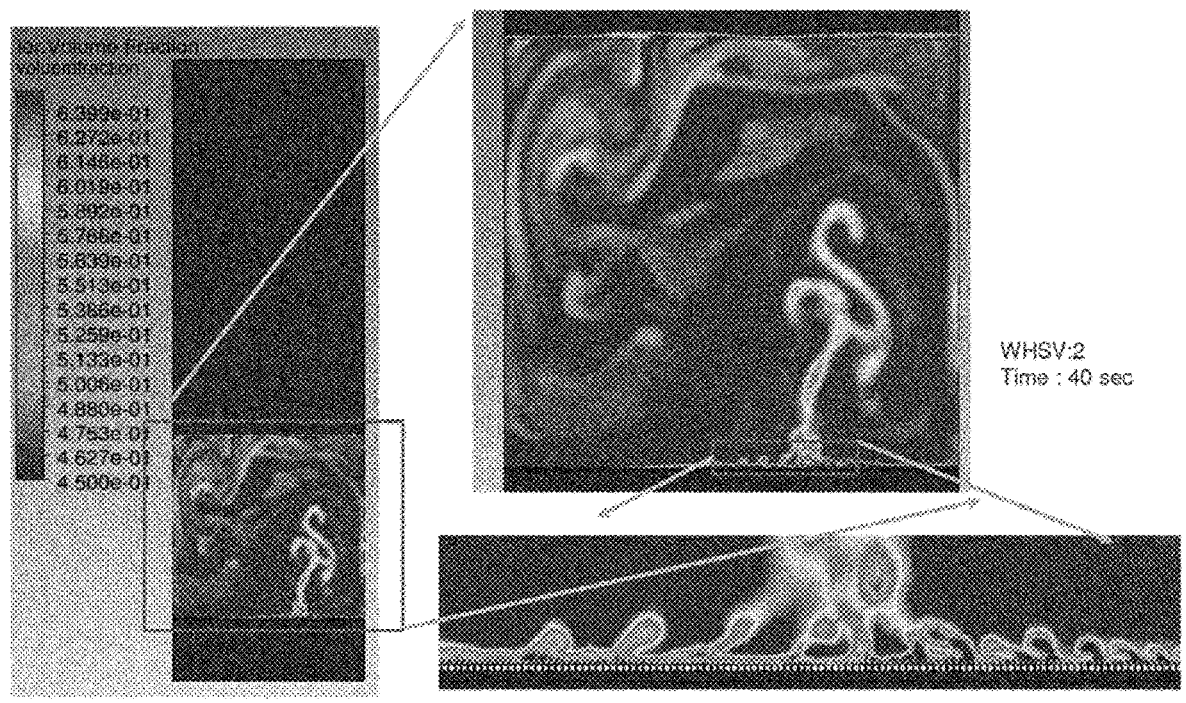
FIG. 4 is an illustration of the volume fraction contours of ion exchange resin in the catalyst bed of the CFD example.
Figure 5:
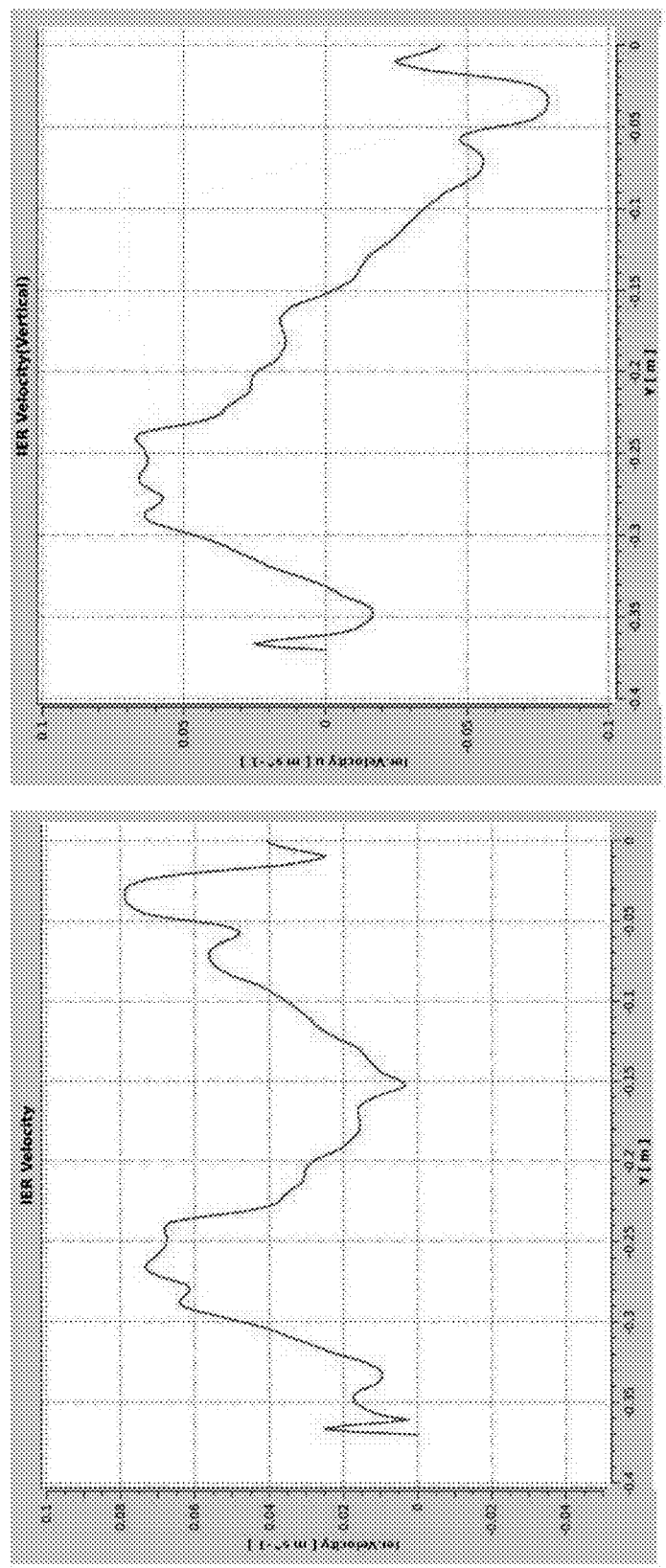
FIG. 5 is an graphical illustration of the ion exchange resin (IER) velocity profiles of the CFD example.

Volume fraction contours of ion exchange resin in the catalyst bed are as shown in FIG. 4. It was observed that the liquid jets that are coming out of the distributor plate slots are merging which leads to a stronger jet formation and that this jet has created significant channelling in the catalyst bed. Ion exchange resin (IER) velocity profiles are as shown in FIG. 5, to illustrate the channelling/recirculation behaviour in the catalyst bed. The graph on the left shows the ion exchange resin velocity magnitude profile at 150 mm above the distributor plate, whereas the graph on the right concerns the ion exchange resin velocity (vertical) profile at 150 mm above the distributor plate. Y=0 m represents the centre axis line of the up-flow reactor, and Y=−0.37 m represents the wall of the up-flow reactor. The wavy velocity pattern actually confirms the presence of strong channels/recirculation flow pattern in the catalyst bed. These figures show that intense recirculation occurred in the catalyst bed. In attempting to quantify the intensity of recirculation the maximum ion exchange resin velocity magnitude in catalyst bed can be divided by the superficial velocity. This yields a value of (0.11/0.000264=) 417.

Figure 6:
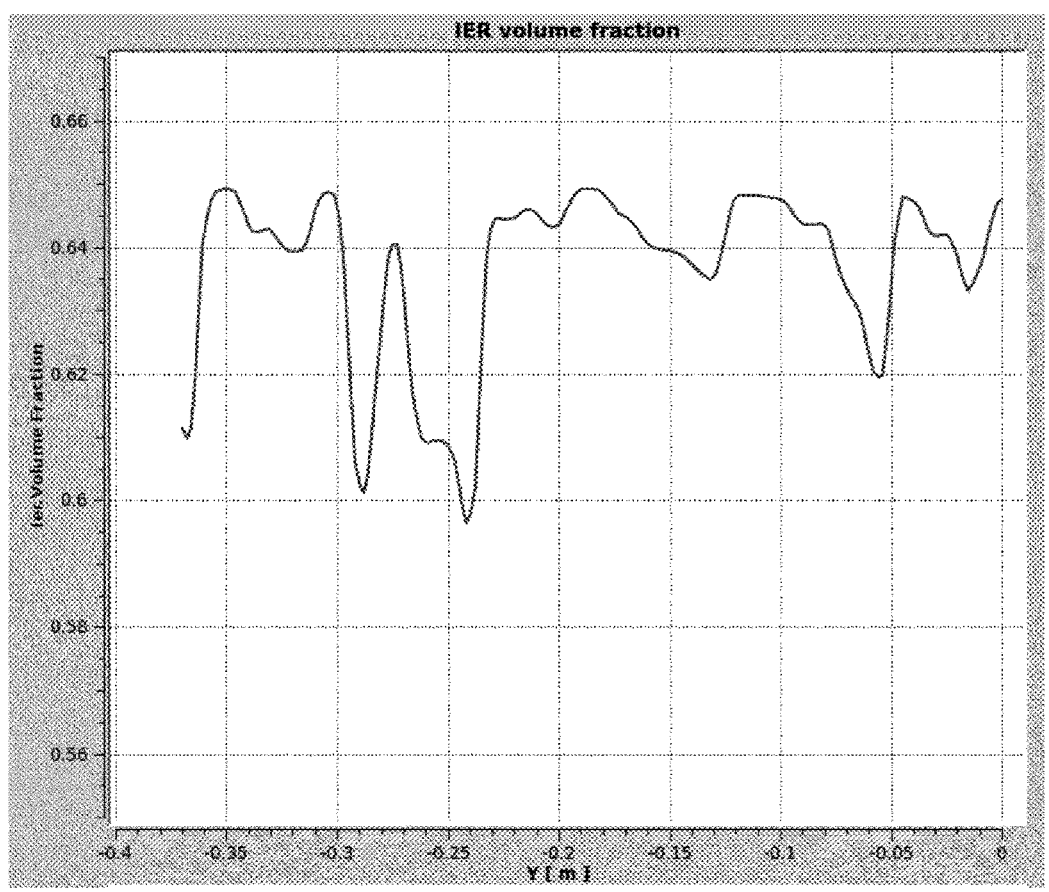
FIG. 6 is a graphical illustration of the ion exchange resin volume fraction profiles of the CFD example.

Ion exchange resin volume fraction profiles are as shown in FIG. 6. The graph shows the ion exchange resin volume fraction profile at 150 mm above the distributor plate. The volume fraction profile indicates significant bed expansion/fluidisation.

Inventive CFD Example

CFD simulations were done in a single stage up-flow reactor using 1000 μm core-shell type of ion exchange resin catalyst particle as described in table 3. Similar CFD framework was followed for both the comparative and inventive examples. The effective density of the core-shell structure is calculated as shown in Table 3 using mass balance approach. Simulation conditions are shown in table 4. A WHSV of 8.3 corresponds to a superficial velocity of 0.0011 m/s. The up-flow reactor used for modelling was the same as in the comparative example.

CFD simulations were done in a single stage up-flow reactor using 1000 μm core-shell type of ion exchange resin catalyst particles as described in table 3. Simulation conditions are as shown in table 4.

TABLE 3

| | |
|---|---|
| core diameter | 600 μm |
| core volume | $1.13 \times 10^{-10}$ m$^3$ |
| core density | 2650 kg/m$^3$ |
| core mass | $3.00 \times 10^{-7}$ kg |
| shell layer thickness | 200 μm |
| shell volume | $4.10 \times 10^{-10}$ m$^3$ |
| shell density | 1182 kg/m$^3$ |
| shell mass | $4.85 \times 10^{-7}$ kg |
| total volume | $5.23 \times 10^{-10}$ m$^3$ |
| total mass | $7.85 \times 10^{-7}$ kg |
| core-shell particle diameter | 1000 μm |
| overall effective density | 1499 kg/m$^3$ |

TABLE 4

| Condition | Value |
|---|---|
| Core-shell catalyst particle density | 1499 kg/m$^3$ |
| Feed density | 1032 kg/m$^3$ |
| Feed viscosity | 0.0019 Pa·s |
| Feed velocity at inlet | 0.0011 m/s |
| Initial bed voidage | 0.35 |

Figure 7:
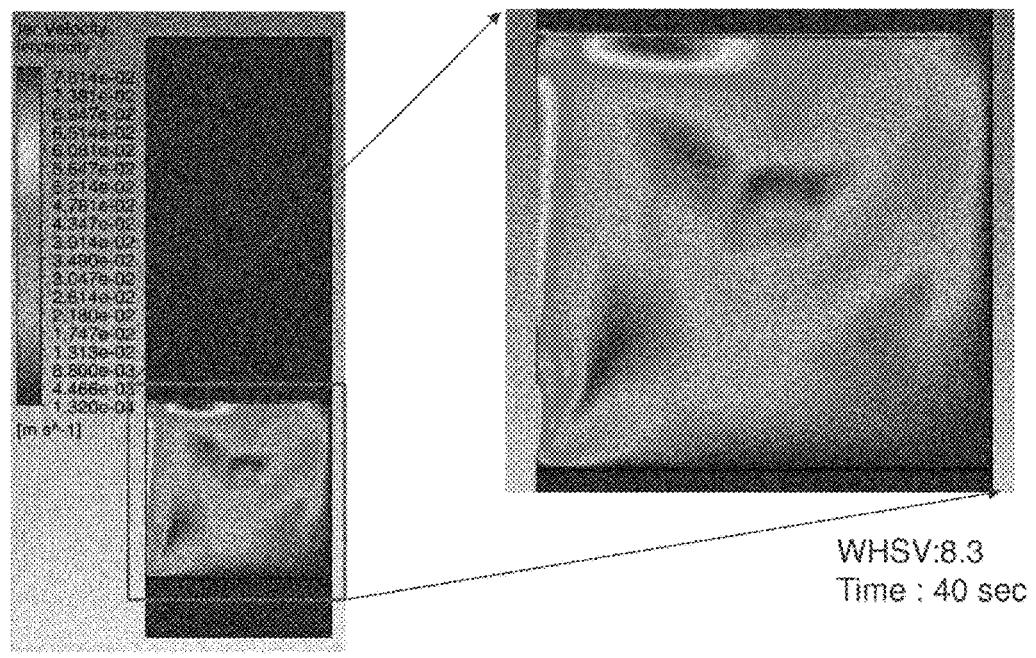
FIG. 7 is an illustration of the volume fraction contours of ion exchange resin in the catalyst bed of the inventive CFD example.

Multiphase CFD simulations were done in a transient mode at WHSV=8.3 and the results at 40 seconds simulation time are shown in FIG. 7. Channelling was noticed in the catalyst bed, although much less than in the comparative example while the WHSV was significantly higher. The chosen simulation condition was probably slightly above bed suspension velocity.

Figure 8:
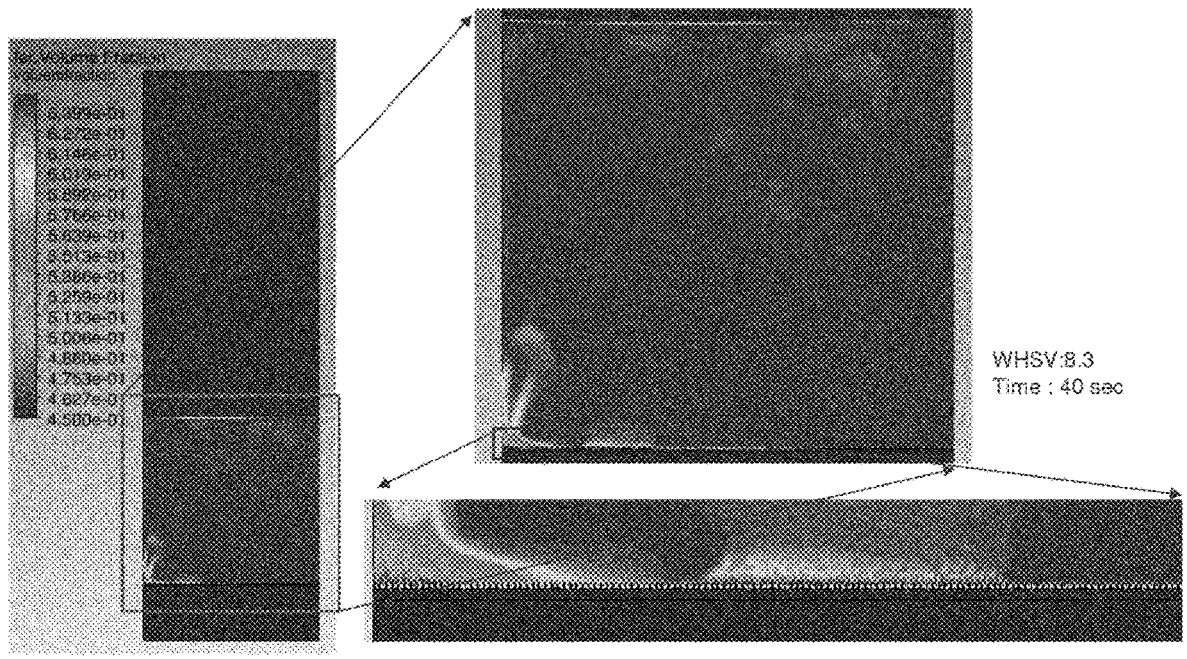
FIG. 8 is an illustration of the volume fraction contours of ion exchange resin in the catalyst bed of the inventive CFD example.
Figure 9:
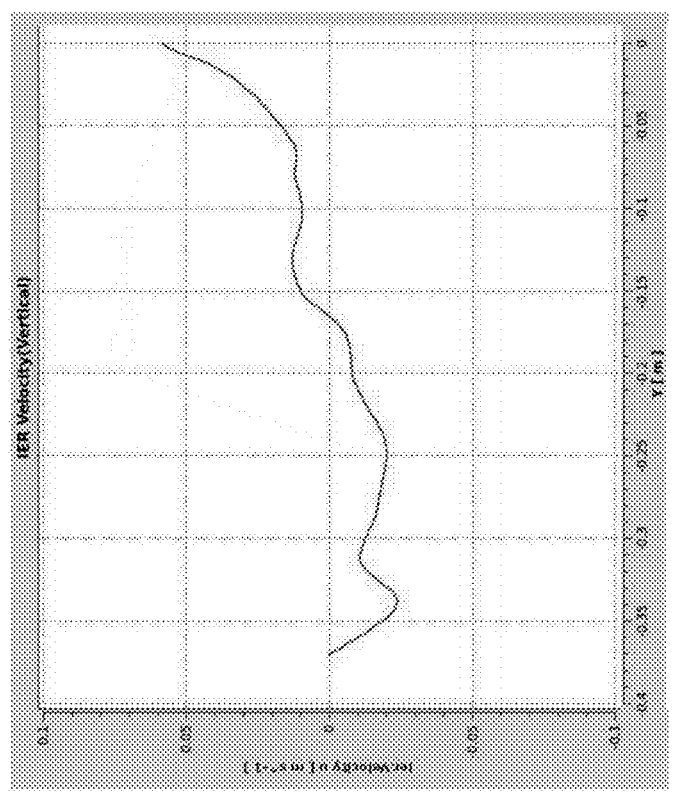
FIG. 9 is a graphical illustration of the ion exchange resin (IER) velocity profiles of the inventive CFD example.
Figure 9:
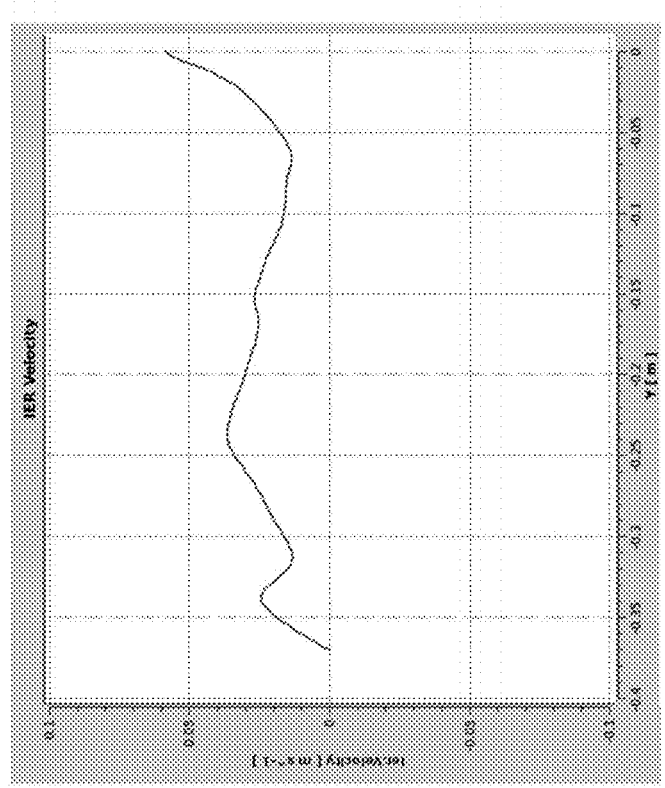

Volume fraction contours of ion exchange resin in the catalyst bed are as shown in FIG. 8. It was observed that smaller jets of some of the slots merged to form channelling at the centre. As compared to FIG. 4, the channelling was much less although WHSV was much higher. Ion exchange resin (IER) velocity profiles are as shown in FIG. 9, to illustrate the channelling/recirculation behaviour in the catalyst bed. The graph on the left shows the ion exchange resin velocity magnitude profile at 150 mm above the distributor plate, whereas the graph on the right concerns the ion exchange resin velocity (vertical) profile at 150 mm above the distributor plate. Y=0 m represents the centre axis line of the up-flow reactor, and Y=−0.37 m represents the wall of the up-flow reactor. The intensity of recirculation may be represented by dividing the maximum ion exchange resin velocity magnitude by the superficial velocity yields a value of (0.08/0.0011=) 73. This is much lower than the value of 417 obtained for the comparative example.

Figure 10:
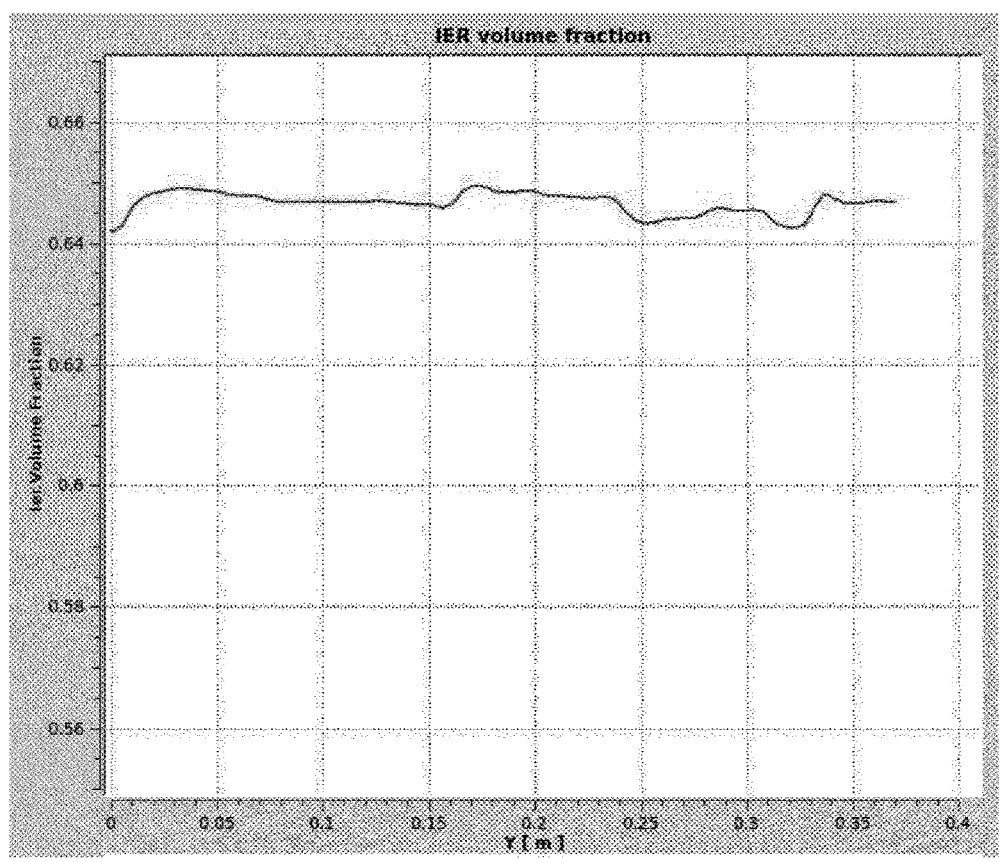
FIG. 10 is graphical illustration of the ion exchange resin volume fraction profile at 150 mm above the distributor plate of the inventive CFD example.

An ion exchange resin volume fraction profile is as shown in FIG. 10. The graph shows the ion exchange resin volume fraction profile at 150 mm above the distributor plate. As can be derived from FIG. 10, the extend of bed expansion/fluidisation is much less than for the comparative example shown in FIG. 6.

Comparing the inventive CFD example with the comparative CFD example shows that the core-shell catalysts of the invention improve the catalyst bed stability by several folds. At a WHSV of 2, fluidisation was observed with normal catalyst. Bed suspension was observed only at WHSV 8 with the core-shell catalyst of the invention. This shows that the catalyst of the invention opens up a broad operating space for high space velocity reactors.

The invention claimed is:

1. A catalyst for the manufacture of a bisphenol from phenol and a ketone, comprising particles having a core and a shell, wherein the shell comprises an ion exchange resin covering the core at least in part and wherein the core has a density that is higher than the density of the ion exchange resin, wherein the core of the particles has a density of at least 2500 kg/m$^3$, wherein the core of the particles has an average particle diameter of 500-1500 μm as determined with microscopy.

2. The catalyst according to claim 1, wherein the core comprises one or more selected from the group consisting of ceramics and metals.

3. The catalyst according to claim 1, wherein the ion exchange resin comprises one or more selected from the group consisting of sulphonated polystyrene copolymers, sulphonated poly(styrene-divinyl-benzene) copolymers, and sulphonated phenol-formaldehyde resins.

4. The catalyst according to claim 1, wherein the shell further comprises a mercaptan promoter.

5. A catalyst for the manufacture of a bisphenol from phenol and a ketone, comprising particles having a core and a shell, wherein the shell comprises an ion exchange resin covering the core at least in part and wherein the core has a density that is higher than the density of the ion exchange resin, wherein the core of the particles has a density of at least 2500 kg/m$^3$, wherein the shell of the particles has an average layer thickness of 100-1000 μm as determined with microscopy.

6. The catalyst according to claim 1, wherein the particles have an average particle diameter of 600-2500 μm as determined with microscopy.

7. The catalyst according to claim 1, wherein the shell of the particles has a density of 800-1500 kg/m$^3$.

8. A method for manufacturing the catalyst of claim 1, comprising the steps of providing core particles and covering an outside surface of the particles at least in part with an ion exchange resin, wherein said core particles have a density that is higher than the density of the ion exchange resin.

9. A catalyst for the manufacture of a bisphenol from phenol and a ketone, comprising particles having a core and a shell, wherein the shell comprises an ion exchange resin covering the core at least in part and wherein the core has a density that is higher than the density of the ion exchange resin, wherein the core of the particles has a density of 2500-4500 kg/m$^3$.

10. The catalyst according to claim 9, wherein the core of the particles has an average particle diameter of 500-1500 μm as determined with microscopy.

11. A method for manufacturing a bisphenol compound, comprising reacting the phenol and the ketone in the presence of the catalyst according to claim 1.

12. The method according to claim 11, wherein the reaction is performed in an up-flow reactor wherein the phenol and the ketone are fed to the reactor at an inlet and bisphenol is extracted at an outlet at a position higher than the inlet.

13. The method according to claim 11, wherein the bisphenol compound is selected from the group consisting of bisphenol A (2,2'-bis(4-hydroxyphenyl)propane), bisphenol S (4,4'-sulphonyldiphenol) and bisphenol F (4,4'-dihydroxydiphenylmethane).

14. A method for manufacturing a bisphenol comprising reacting a phenol and a ketone in the presence of the catalyst according to claim 1, wherein the reaction is performed in an up flow reactor wherein the phenol and the ketone are fed to the reactor at an inlet and bisphenol is extracted at an outlet at a position higher than the inlet.

\* \* \* \* \*